(12) United States Patent
Martin et al.

(10) Patent No.: US 9,480,261 B1
(45) Date of Patent: Nov. 1, 2016

(54) **INSECTICIDAL STRAIN OF *SERRATIA* FOR CONTROL OF BROWN MARMORATED STINK BUG (BMSB), *HALYOMORPHA HALYS***

(71) Applicant: The United States of America, as Represented by the Secretary of Agriculture, Washington, DC (US)

(72) Inventors: Phyllis A. Martin, Lanham, MD (US); Terrence A. Price, Bowie, MD (US); Dawn E. Gundersen-Rindal, Silver Spring, MD (US)

(73) Assignee: The United States of America, as Represented By the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/298,048

(22) Filed: Jun. 6, 2014

(51) Int. Cl.
*A01N 63/00* (2006.01)
*C12R 1/425* (2006.01)

(52) U.S. Cl.
CPC .............. *A01N 63/00* (2013.01); *C12R 1/425* (2013.01)

(58) Field of Classification Search
None
See application file for complete search history.

(56) References Cited

U.S. PATENT DOCUMENTS

2003/0068304 A1\* 4/2003 Mattingly ............ A01N 25/006
424/93.4

OTHER PUBLICATIONS

Chang, et al. "Development of natural anti-tumor drugs by microorganisms", Journal of Bioscience and Bioengineering 2011, vol. 111, pp. 501-511.\*
Torres-Barragan et al., "Studies on the entomopathogenicity and bacterial associates of the nematode Oscheius carolinensis", Biological Control 2011, vol. 59, pp. 123-129.\*
Chang, C.-C. et al., "Development of Natural Anti-Tumor Drugs by Microorgnisms", Journal of Bioscience and Bioengineering 2011, vol. 111, pp. 501-511.
Tu, S. et al., "Expression and Characterization of the Chitinases from Serratia Marcescens GEI Strain for the Control of Varroa Destructor, a Honey Bee Parasite", Journal of Inverterate Pathology 2010, vol. 104, pp. 75-82.

\* cited by examiner

*Primary Examiner* — Renee Claytor
*Assistant Examiner* — Michelle F Paguio Frising
(74) *Attorney, Agent, or Firm* — John D. Fado; G. Byron Stover

(57) ABSTRACT

Disclosed are biocontrol agents for the control of insects (e.g., *Halyomorpha halys*), in particular, to a certain *Serratia* strain capable of killing insects such as *Halyomorpha halys*. More specifically, disclosed is the *Serratia* strain NRRL B-50575. Also disclosed is a biocontrol strategy whereby insects (e.g., BMSB) are exposed to the *Serratia* strain NRRL B-50575 as a method for killing insects.

3 Claims, 6 Drawing Sheets

SEQUENCE LISTING

```
<160> NUMBER OF SEQ ID NOS: 1

<210> SEQ ID NO 1
<211> LENGTH: 1225
<212> TYPE: DNA
<213> ORGANISM: Unknown
<220> FEATURE:
<223> OTHER INFORMATION: Tentatively Serratia marcescens

<400> SEQUENCE: 1
tttgcaaccc actcccatgg tgtgacgggc ggtgtgtaca aggcccggga acgtattcac      60
cgtagcattc tgatctacga ttactagcga ttccgacttc atggagtcga gttgcagact     120
ccaatccgga ctacgacata ctttatgagg tccgcttgct ctcgcgaggt cgcttctctt     180
tgtatatgcc attgtagcac gtgtgtagcc ctactcgtaa gggccatgat gacttgacgt     240
catccccacc ttcctccagt ttatcactgg cagtctcctt tgagttcccg gccgaaccgc     300
tggcaacaaa ggataagggt tgcgctcgtt gcgggactta acccaacatt tcacaacacg     360
agctgacgac agccatgcag cacctgtctc agagttcccg aaggcaccaa tccatctctg     420
gaaagttctc tggatgtcaa gagtaggtaa ggttcttcgc gttgcatcga attaaaccac     480
atgctccacc gcttgtgcgg gcccccgtca attcatttga gttttaacct tgcggccgta     540
ctccccaggc ggtcgattta acgcgttagc tccggaagcc acgcctcaag ggcacaacct     600
ccaaatcgac atcgtttaca gcgtggacta ccagggtatc taatcctgtt tgctccccac     660
gctttcgcac ctgagcgtca gtcttcgtcc agggggccgc cttcgccacc ggtattcctc     720
cagatctcta cgcatttcac cgctacacct ggaattctac ccccctctac gagactctag     780
cttgccagtt tcaaatgcag ttcccaggtt gagcccgggg atttcacatc tgacttaaca     840
aaccgcctgc gtgcgcttta cgcccagtaa ttccgattaa cgcttgcacc ctccgtatta     900
ccgcggctgc tggcacggag ttagccggtg cttcttctgc gagtaacgtc aattgatgag     960
cgtattaagc tcaccacctt cctcctcgct gaaagtgctt tacaacccga aggccttctt    1020
cacacacgcg gcatggctgc atcaggcttg cgcccattgt gcaatattcc ccactgctgc    1080
ctcccgtagg agtctggacc gtgtctcagt tccagtgtgg ctggtcatcc tctcagacca    1140
gctagggatc gtcgcctagg tgagccatta ccccacctac tagctaatcc catctgggca    1200
catctgatgg caagaggccc gaagg                                          1225
```

INSECTICIDAL STRAIN OF *SERRATIA* FOR CONTROL OF BROWN MARMORATED STINK BUG (BMSB), *HALYOMORPHA HALYS*

REFERENCE TO RELATED APPLICATION

This application claims the benefit of U.S. Provisional Application No. 61/595,783, filed 7 Feb. 2012, which is incorporated herein by reference in its entirety.

BACKGROUND OF THE INVENTION

Disclosed are biocontrol agents for the control of insects (e.g., *Halyomorpha halys*), in particular, to a certain *Serratia* strain capable of killing insects such as *Halyomorpha halys*. More specifically, disclosed is the *Serratia* strain NRRL B-50575. Also disclosed is a biocontrol strategy whereby insects (e.g., BMSB) are exposed to the *Serratia* strain NRRL B-50575 as a method for killing insects.

The brown marmorated stink bug (BMSB), *Halyomorpha halys* (Hemiptera: Pentatomidae), is an insect native to China, Japan, Taiwan, and Korea. It is an exotic insect pest that invaded the United States in 2001 (Hoebeke, E. R., and M. E. Carter, Proc. Entomol. Soc. Wash., 105: 225-237 (2003); Funayama, K., Applied Entomology and Zoology, 39(4): 617-623 (2004); Funayama, K., Japanese Journal of Applied Entomology and Zoology, 49(4): 265-268 (2005); Funayama, K., Japanese Journal of Applied Entomology and Zoology, 51(3): 238-240 (2007); Son, J, K, et al., Acta Horticulturae, pages 325-330 (2009)). Since then it has spread to more than 33 states and has been found to feed on over 60 host plants, including forest trees, ornamentals, soybeans, and garden vegetables (Hoebeke and Carter 2003; Funayama 2004; Funayama 2005; Funayama 2007; Son et al. 2009). Damage to crops from BMSB in mid-Atlantic States has now reached critical levels (Marder, J., 2001, Stink Bug Invasion: Is a Wasp the Solution to Save Valued Crops? http://www.pbs.org/newshour/rundown/2011/05/fighting-the-stink-bug.html, Jun. 8, 2011). BMSB has caused serious damage to peach and apple crops in southeastern PA with some growers loosing over 60 percent of their crop (Sun-Gazette, Brown marmorated stink bug update, http://www.sungazette.com/page/content.detail/id/561129/Brown-marmorated-stink-bug-update.html-?nav=5014, Jun. 8, 2011).

The BMSB is thought to have been introduced to the United States via packaging crates in the late 1990s, and was first spotted in Pennsylvania in 1998. While the BMSB is not a problem in Asia, due to natural enemies, there are currently no effective ways of combating the insect in the U.S.

Thus there is a need for biocontrol of insects like BMSB.

SUMMARY OF THE INVENTION

We have isolated the *Serratia* strain NRRL B-50575, and discovered that this strain can kill insects such as BMSB. We have provided an isolated *Serratia* strain NRRL B-50575 which can act as a biocontrol agent for insects such as BMSB. We have also provided a method for biocontrol of insects such as BMSB.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

Deposit of the Microorganism

*Serratia* strain, designated NRRL B-50575, has been deposited under the provisions of the Budapest Treaty on 22 Sep. 2011 (NRRL B-50575) with the U.S.D.A. Agricultural Research Service Patent Culture Collection (National Center for Agricultural Utilization Research, 1815 N. University Street, Peoria, Ill., 61604).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3(*a*) is field collected BMSB and FIG. 3(*b*) is colony reared BMSB.

DETAILED DESCRIPTION OF THE INVENTION

Figure 1:
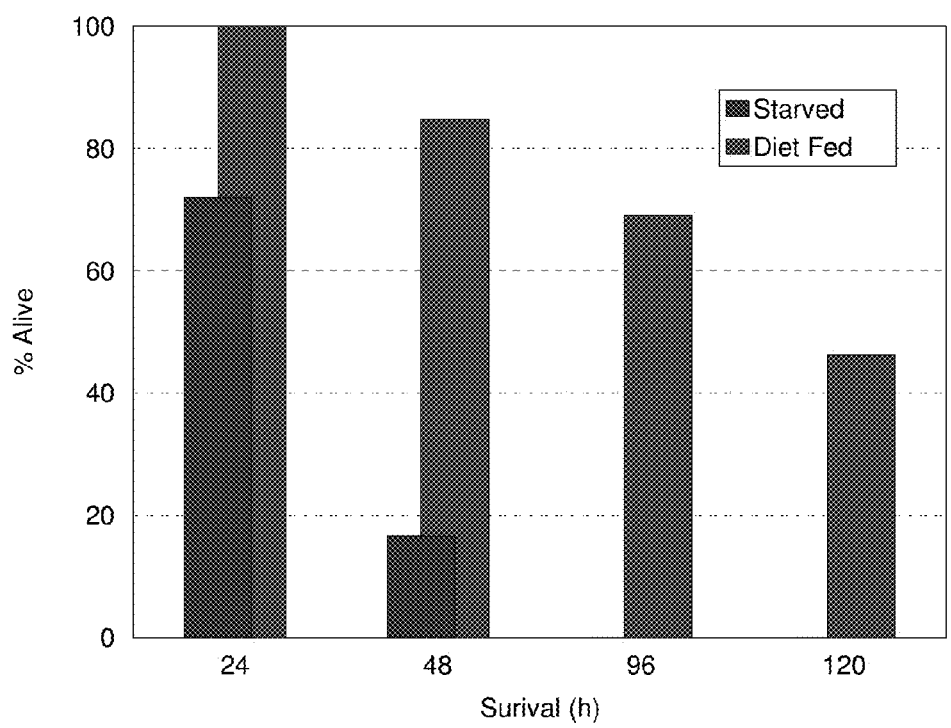
FIG. 1 shows survival data of feeding assay for BMSB as described below.

We have identified *Serratia* strain NRRL B-50575 that kills insects such as BMSB.

*Chromobacterium subtsugae* (Martin, P. A. W., et al., Internatl. J. System. Evolut. Micrbiol., 57: 993-999 (2007)) is pathogenic to the southern green stink bug (Martin, P. A. W., et al., J. Econ. Entomol., 100: 680-684 (2007)), and this was one of the first pathogens tested against the BMSB. In a BMSB feeding test we tested *C. subtsugae* PRAA4-1 (NRRL B-30655, U.S. Pat. No. 7,224,607), *Serratia marscesens* BF1, and *Bacillus thuringiensis* IBL 999 (NRRL B-18195), known to be toxic to some species of insects. *C. subtsugae* had some effect on BMSB. During this test there was high mortality in the negative control, that is BMSB that were fed only water were dying. We thought that a pathogen might be the cause. Many of the insects that were dying had abdomens that were a bright crimson color rather than the natural tan color. A bacteria strain (NRRL B-50575), which produced a diffusible pink pigment, was isolated from the gut of several insects with red abdomens. Through Koch's postulates, the bacterial strain was confirmed as being pathogenic to BMSB.

The taxonomic position of NRRL B-50575 is uncertain. Several identification procedures have been performed, including a fatty acids analysis, phenotypic tests, and molecular 16S rRNA gene sequencing. A BLAST search (performed at the National Center for Biotechnology Information NCBI web site which compares a DNA sequence with others in the data base) on the 16S rDNA gene found three *Serratia* species with 99% similarity: *S. marcescens*, *S. nematodiphilia*, and *S. rubidaea*. Biolog GEN III identifies NRRL B-50575 as *Serratia marcescens* with 0.66 similarity as possibly does MALDI-TOF (Matrix Assisted Laser Desorption/Ionization—Time Of Flight) which looks at ribosomal proteins. Fatty acid analysis identifies NRRL B-50575 as other species with low similarities. NRRL B-50575 was isolated from environmentally collected BMSB and shown to kill insects such as the brown marmorated stink bug.

Disclosed is a method of killing insects, involving exposing (or treating) insects or an object (e.g., insects, plants, fruit trees) or area (e.g., soil, house) in need of such treatment with an insect killing effective amount of *Serratia* strain NRRL B-50575, and optionally a carrier or carrier material. The terms "object" or "area" as used herein include any place where the presence of target pests is not desirable, including any type of tree or crop. The amount of the compositions used will be at least an effective amount. The term "effective amount," as used herein, means the minimum amount of the compositions needed to kill the insects when compared to the same area or object which is untreated. Of course, the precise amount needed will vary in accordance with the particular composition used; the type of area or object to be treated; and the environment in which the area or object is located. The precise amount of the composition can easily be determined by one skilled in the art given the teaching of this application. For example, one skilled in the art could follow the procedures utilized below; the composition would be statistically significant in comparison to a negative control. The composition may or may not contain a control agent for insects, such as an insecticide known in the art to kill insects. Other compounds (e.g., insect attractants or biocontrol agents known in the art) may be added to the composition provided they do not substantially interfere with the intended activity and efficacy of the composition; whether or not a compound interferes with activity and/or efficacy can be determined, for example, by the procedures utilised below.

The carrier or carrier material may be, for example, agronomically or physiologically or pharmaceutically acceptable carriers or carrier materials. The carrier or carrier material as used herein is defined as not including the body of an insect (e.g., *Halyomorpha halys*).

A single application will suffice under optimum conditions, with mortality occurring rapidly, but under suboptimum conditions, either higher concentrations or multiple applications may be necessary.

Herein an insect biocontrol composition refers to a microbial preparation wherein the microbes comprise, consist essentially of, or consist of *Serratia* strain NRRL B-50575. The insect biocontrol composition includes *Serratia* strain NRRL B-50575 on agriculturally acceptable carriers (e.g., insect food) which may be any carrier which the *Serratia* strain can be attached and are not harmful to plants which are treated with the composition.

The *Serratia* especially useful in the present invention are strains possessing the identifying characteristics of *Serratia* strain NRRL B-50575. These characteristics include the following: (1) the ability to kill insects such as BMSB; (2) can cause the abdomens of male BMSB to change from a tan hue to pink/red/crimson; (3) does not oxidize α-cyclodextrin, D-arabitol, i-erythritol, α-lactose, α-D-lactose lactulose, L-rhamnose, turanose, D-galactonic acid lactone, D-glucosaminic acid, α-hydroxy butyric acid, α-keto butyric acid, α-keto glutaric acid, propionic acid, alaninamide, glycyl-L-aspartic acid, glycyl-L-glutamic acid, L-ornithine, L-phenyl alanine, L-threonine, phenyl ethylamine, L-aspartic acid, succinic acid, D-trehalose, mono-methyl succinate, β-hydroxy butyric acid, and uridine; (4) resistance to antibiotics: ampicillin (resistant), vancomycin (resistant), erythromycin (resistant), triple sulfa (resistant), tetracycline (intermediate), kanamycin (susceptible), neomycin (susceptible), and chloramphenicol (intermediate); (5) produces urease; (6) produces lipase; (7) has a growth temperature optima of 30° C.; (8) pigment diffuses into the growth medium and is produced at temperatures under 25° C. in L agar with 0.5% NaCl, does not produce pigment at above 30° C., spectral properties of the pigment: peaks at 605, 510, and 410 nm; (9) does not produce pigment when grown at 25° C. on sugar agar where the sugar is trehalose, fructose, sucrose, melibose, lactose, galactose, arabinose, salicin, esculin or mannose; (10) grows on 8% and 10% KCl; (11) fatty acid composition: 14:0 (about 4.47%; about 3.73 times more than ATCC 13880), 15:0 (0%), 16:0 (about 31.03%; about 71.8% of that of ATCC 13880), 16:1 (about 14.62%; about 2.81 times more than ATCC 13880), 17:1 (about 0.18%; about 18% that of ATCC 13880), cyclo 17:0 (about 12.2%; about 38.9% that of ATCC 13880), 18:0 (0%; compared to about 1.2% for ATCC 13880), 18:1 (about 14.67%; about 1.33 times more than ATCC 13880), cyclo 19:0 (about 2.53%; about 46.9% that of ATCC 13880); (12) grows at pH 4; (13) is a gram-facultative aerobe, motile rods averaging 1 micron×2.5 microns, capable of growth between 4° C. and 40° C., grows on L-agar (1% tryptone, 0.5% yeast extract, 0.5% sodium chloride, 1% agar) producing circular, opaque, raised, smooth, glossy dark tone of pink colonies 2-3 mm in diameter after aerobic incubation for 1-2 days at 25° C., pink pigment diffuses into the medium at 2-3 days. See also the identifying characteristics in Tables 2-8. Especially important identifying characteristics of *Serratia* strain NRRL B-50575 include the following: (1) produces diffusible pigment, (2) grows on D-serine and D-galactose as sole carbon source, (3) makes acid from trehalose, (4) pigment not produced by growth on sugars, (5) produces urease and lipase, and (6) pathogenic to BMSB (*Halyomorpha halys*); also (7) has a growth temperature optima of 30° C. and (8) spectral properties of the pigment: peaks at 605, 510, and 410 nm.

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

*H. halys* Collection: BMSB were collected at dusk during July 2011 in Bowie, Md. To catch the insects, they were simply scooped into a container made out of a soda bottle, and as a result of the trap's funnel-like shape, they were unable to escape. The stink bugs were kept in individual Petri dishes and fed organic apples for a week before testing.

Feeding Assay: The next large step in the research was to find out a way to administer a pathogen to the insects. Artificial, freeze-dried diets (Martin, P. A. W., et al., J. Econ. Entomol., 97: 774-780 (2004)) must be rehydrated using a liquid, so this was done by using a suspension of the pathogen. The only problem with this, however, was the fact that there was no available stink bug diet during the time of research. Because of this, a way to administer the pathogen to the insects needed to be found, so several feeding assays were set up. The first assay was a choice test, which would determine if there were any artificial diets that the insects would feed on instead of a slice of apple. To do this, several Petri dishes were set up. Each dish contained a stink bug, a slice of apple, and one type of diet. The types used consisted of freeze-dried squash, southern corn rootworm larvae diet, tobacco horn worm diet, and diamond back moth diet (Table 1).

Bioassay: In order to determine just how effective NRRL B-50575 actually was against BMSBs, a bioassay was required. A bioassay test is a series of comparisons and trials that show the effects of several different agents (in this case, bacterial pathogens) on a certain organism. The first assay that was set up consisted of 9 Petri dishes, each with 2 diet pellets (Martin, 2004) and a stink bug within. Three of the pellets were rehydrated with a suspension of *Chromobacterium subtsugae* (Martin et al., Internatl. J. System. Evolut. Micrbiol., 57: 993-999 (2007)), 3 were rehydrated with *Serratia marcescens* (Farrar, R. R., Jr., et al., J. Entomol. Sci., 36: 380-390 (2001)), and the last 3 were rehydrated with a strain of *Bacillus thuringiensis*, IBL 999 (U.S. Pat. No. 4,950,471). Once NRRL B-50575 was discovered, however, the agents used in the bioassay were altered. Eventually, about 8 dishes were used for each rehydration agent, and 8 cotton wicks with just water were used. The rehydration agents used consisted of a NRRL B-50575 suspension, a *C. subtsugae* suspension, and sterile water.

Bacterial Isolation: There were several steps that had to be taken in order to isolate the bacteria from the stink bugs. Firstly, to assure that the pathogen that was to be isolated was not simply on the outside of the insect, the surface of the BMSB had to be sterilized. The insect was rinsed with a 70% ethanol solution, and then rinsed clean using sterile water. After this, the insect was put into 5 mL of sterile water in a WhirlPak®, and ground up using a stomacher blender on high for 60 seconds (Martin, P. A. W., et al., Biocont. Sci. Technol., 18: 291-305 (2008)). This suspension was then titered onto L-agar plates. The plates were incubated over night at 25° C. and the bacteria from single colonies were then able to be identified.

Koch's Postulates: Koch's postulates, first theorized by Robert Koch (Black, J. C., Microbiology: Principles and Applications, 3rd Ed., 1996, Prentice-Hall Inc., Upper Saddle River, N.J.), were essentially used to confirm the pathogenic properties of NRRL B-50575. After the NRRL B-50575 was isolated from BMSB, the initial culture was grown up on L-agar (1% tyrptone, 0.5% yeast extract, 0.5% NaCl, and 1% agar) for 48 hours at 25° C., harvested in water, applied to diet pellets, and fed back to two more stink bugs. After several days, these stink bugs died and the same methods previously used to isolate the bacteria from dead insects were then use to isolate the bacteria from these insects. Finally, the bacteria that were isolated at the end of Koch's postulates were identified by the same tests as NRRL B-50575, TPSB-08, TPSB-09, and BF1. This was done to confirm that the bacteria were the same.

Bacterial Identification: To identify NRRL B-50575, as well as multiple other bacteria, several identification procedures were utilized. First the bacterial strains were Gram stained or tested for cell lysis with 3% KOH. The next test used for identification was a series of biochemical profiles in order to see what substrates the bacteria used or fermented. To do this, three separate colonies of NRRL B-50575 were cultured on 3 different dots of agar (Martin, P. A. W., et al., BioTechniques., 3: 386-392 (1985)) and incubated for 24 hours at 25° C. After there was sufficient growth on each dot, 12 different sets of agar dots, each containing a different substrate (e.g., glucose, mannitol, arabinose, casein, cellibiose, starch, lecithin, sucrose, salicin, esculin, mannose, and sheep blood), were inoculated using them. In addition to these agar dots, several sugars (e.g., melibiose, trehalose, lactose, fructose, galactose, maltose, and xylose) and peptone agar (to be used for a urease test) were inoculated.

Biochemical Tests with Biolog System: Multiple biochemical profiles using a Biolog system (Palo Alto, Calif.) were performed. This procedure uses 96 wells with a different chemical or substrate in each, and a suspension of bacteria was used to inoculate each well. If the bacteria in any given well oxidized the chemical/substrate in said well, the bacteria produced tetrazolium purple and caused a permanent change in the color of the suspension. Two versions were used, one for Gram+ organisms and the new GEN III version.

Antibiotic Susceptibility: Two agar plates were streaked for growth with NRRL B-50575, and 8 paper discs, each soaked in a different antibiotic, were placed on the agar, with 4 discs on each plate. Disks containing the following antibiotics were used/obtained from Remel (Lenexa Kans.): ampicillin (10 μg), chloramphenicol (30 μg), erythromycin (30 μg), kanamycin (30 μg), neomycin (30 μg), tetracycline (30 μg), triple sulfa (300 μg) and vancomycin (30 μg). The plates were incubated for 24 hours at 25° C., and after this incubation period the zone of inhibition around each disc was measured.

Molecular Identification: The final 2 tests used to determine the identity of the bacteria consisted of a fatty acids analysis (MIDI, Inc. (2002), Sherlock Microbial Identification System Version 4.5. MIS Operating Manual July, MIDI, Inc., Newark, Del.) used to ascertain the relatedness of the bacteria to other known species, and a 16S rRNA gene sequencing procedure (Lee, I. M., et al., Mol. Plant Pathol., 83: 834-842 (1993) used to sequence the ribonucleic acid in the bacteria.

A typical urea media by weight contains 0.2% Bacto peptone, 0.1% Glucose, 0.5% sodium chloride, 0.2% potassium phosphate (monobasic), 2.0% urea and 1 ml (0.2% phenol red), which is the typical urea media we used. However, NRRL B-50575 also produced urease in a media containing 0.1% yeast extract, 0.91% monopotassium phosphate, 0.95% disodium phosphate, 2.0% urea, 0.01% phenol red. If we use this highly buffered recipe then there is no question of BF1 producing a urease. The 2 media were used for differentiation of other bacteria from one another, a weak urease with the 1st poorly buffered medium and a strong urease produced in the more highly buffered 2nd medium.

L-agar by weight contains 1% tryptone, 0.5% yeast extract, 0.5% NaCl, and 1% agar. A typical lipid containing media is an egg yolk agar. 0.1% peptone, 1% mannitol, 02.2% sodium chloride, 0.1% magnesium sulfate, 0.25% di-sodium hydrogen phosphate, 0.025% potassium dihydrogen phosphate, 1% sodium pyruvate, 0.012% bromothymol blue 1% agar, 5 ml of sterile egg yolk emulsion is added after autoclaving (we used fresh (less than 24 h old) egg yolks at 3 per 500 ml of media).

Results. Survival on Diet: From the feeding assay it was discovered that the BMSB will feed on apple as well as an artificial diet (2002 baseline diet without antibiotics) intended for the southern corn rootworm (Pleau, M. J., et al., Entomol. Experimet. Appl., 105: 1-11 (2002). At the beginning of the choice test, the BMSB all fed on the apple (2-3 h). After 24 hours the BMSB in the apple-corn rootworm diet plates were feeding on the diet as well as the apple. The BMSB, as a sucking insect, ingested the liquid from the diet. The preliminary feeding assay not only informed us that the southern corn rootworm diet kept the BMSB hydrated, but it provided them with nutrients. In the assay, several insects fed on the diet, several fed on apple, and several were starved. The starved insects all died within a matter of days, while the majority of the insects feeding on the artificial diet lived as long as those that were feeding on the apple. Using Proc LIFEreg in SAS (SAS Institute Inc., 2011, SAS Online-Doc7. Version 9.2. SAS Institute Inc., Cary, N.C.) the starved insects died significantly sooner than the diet fed insects ($\chi2=47.3$; $P<0.0001$). The bioassay can last up to 96 h with good survival in the diet fed insects.

Figure 2:
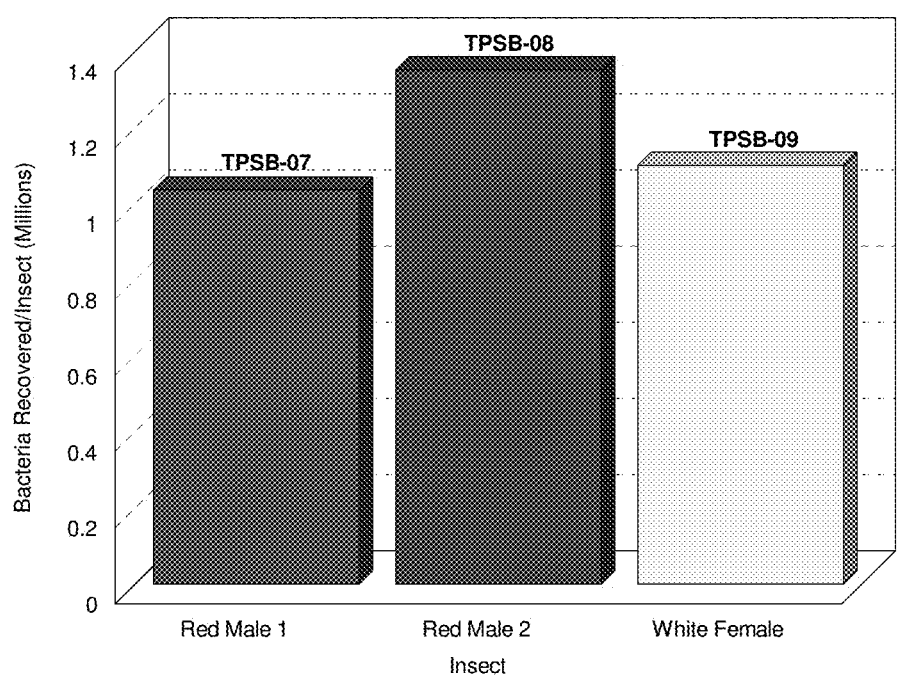
FIG. 2 shows bacterial titers from dead BMSB as described below.

Isolation of Pink Bacteria: Out of the group of BMSB collected one night, the group was split in half. One half was kept in a communal container, and the other half of the insects were placed in individual containers. Of the insects in the communal container, all died over the next 48 h, while only a couple of the individually contained insects perished. NRRL B-50575 (TPSB-07), TPSB-08, and TPSB-09 were then isolated from three individual dead insects from the communal container (FIG. 2). The bacteria from each insect were a single type, in contrast to bacteria isolated from healthy insects which formed several different types of colonies. Insects of different sexes were chosen due to the fact that in the case of C. subtsugae and the southern green stink bug, the two sexes have different sensitivities to the pathogen (Martin, J. Econ. Entomol., 100: 680-684). There was a significant difference in the weight of the sexes, with females ($95.05\pm3.2$ mg) being both larger and heavier than the males ($56.04\pm1.6$ mg), but this did not have an effect on the recovery of bacteria per insect. According to the 16S rRNA gene sequencing, the healthy insects yielded *Pantoea agglomerans, Leclercia adecarboxylata, Acinetobacter baylyi*, and *Stenotrophomonas chelatiphaga*, while the dead insects from this set solely yielded the pink bacteria.

Figure 3A:
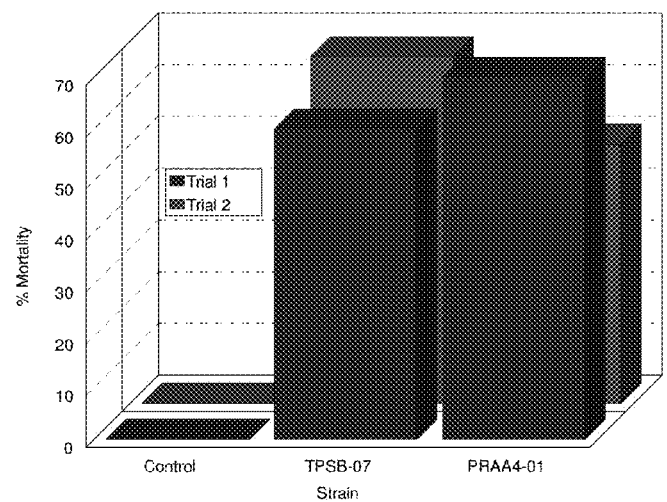
FIG. 3(*a*) and FIG. 3(*b*) shows a comparison of the effects of NRRL B-50575 (*Serratia* strain NRRL B-50575) and *C. subtsugae* PRAA4-1 as described below.
Figure 3B:
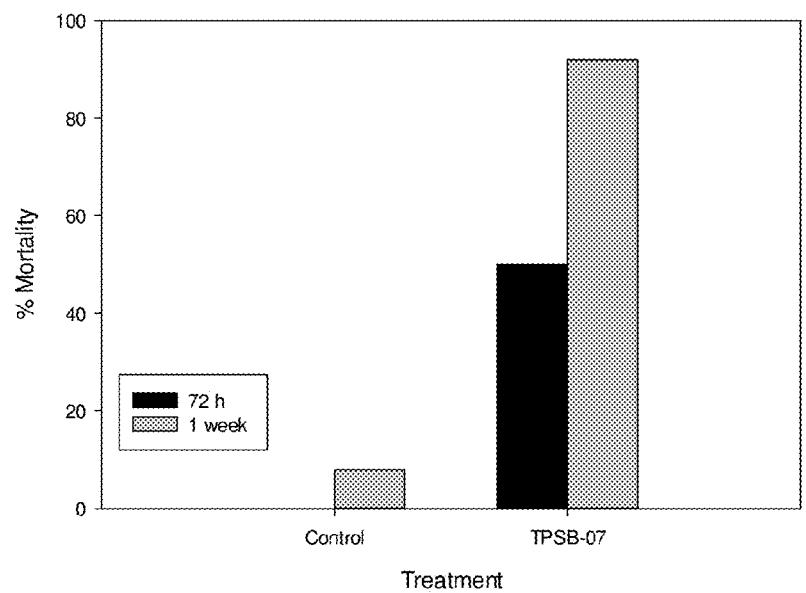

An assay to determine the effectiveness of NRRL B-50575 (TPSB-07) vs. PRAA4-1 was then set up in order to compare the effectiveness of the two pathogens (FIG. 3). In two assays against field collected insects NRRL B-50575 killed about 60% of the insects in 72 h with no control mortality. In an assay against colony reared BMSB, NRRL B-50575 killed 91% of the adult BMSB in a week with 8% control mortality (FIG. 3a); it may have taken longer to kill in the colony assay in the winter because all the stink bugs did not feed right away as they did in the summer. NRRL B-50575 was also effective against $2^{nd}$ instar nymphs with 87.5% kill within one week, while control mortality was 15-20%.

NRRL B-50575 was also tested against *Aedes aegypti* mosquito larvae and diamondback moth larvae (*Plutella xylostella*) and there was no mortality, suggesting that NRRL B-50575 is not a general insect pathogen.

Bacterial Identification: Through the KOH test, NRRL B-50575 was first determined to be Gram negative. The second feature of the bacteria was that it was not only pink, but it seemed to be producing a pink pigment that was diffusing into the media. The 16S rRNA gene sequencing sequenced the DNA of the 16S rRNA gene and showed that NRRL B-50575 was 99% similar to *Serratia marcescens*. In comparison to ATCC 13880 there are three changes in the 16 S rRNA gene: at position 666 (NRRL B-50575 had C, ATCC 13880 had G), at 695 (NRRL B-50575 had G, ATCC 13880 had C), and at 960 (NRRL B-50575 had G, ATCC 13880 had A). The nucleotide "G" at position 960 (of 1225) in the 16S sequence for NRRL B-50575 was a nucleotide "A" in *Serratia marcescens* subsp *marcescens* (strain NBRC 102204) and many other closely related *Serratia* species. The following is the full length 16S sequence for NRRL B-50575: TTTGCAACCCACTCCCATGGTGT-GACGGGCGGTGTGTACAAGGCCCGGGAACGTATT CACCGTAGCATTCTGATCTACGATTACTAGCGATTC-CGACTTCATGGAGTCGAGTTGC AGACTCCAATC-CGGACTACGACATACTTTATGAGGTCCGCTT-GCTCTCGCGAGGTCG CTTCTCTTTGTATATGCCATTGTAGCACGTGTG-TAGCCCTACTCGTAAGGGCCATGAT GACTTGACGT-CATCCCCACCTTCCTCCAGTTTATCACTGGCA-GTCTCCTTTGAGTTCC CGGCCGAACCGCTGGCAACAAAGGATAAGGGTT-GCGCTCGTTGCGGGACTTAACCCA ACATTTCA-CAACACGAGCTGACGACAGCCATGCAGCACCT-GTCTCAGAGTTCCCG AAGGCACCAATCCATCTCTGGAAAGTTCTCTGGAT-GTCAAGAGTAGGTAAGGTTCTT CGCGTTGCATC-GAATTAAACCACATGCTCCACCGCTTGTGCGGGC-CCCCGTCAATTCA TTTGAGTTTTAACCTTGCGGCCGTACTCCCCAG-GCGGTCGATTTAACGCGTTAGCTCC GGAAGC-CACGCCTCAAGGGCACAACCTCCAAATCGA-CATCGTTTACAGCGTGGACTA CCAGGGTATCTAATCCTGTTTGCTC-CCCACGCTTTCGCACCTGAGCGTCAGTCTTCGT CCAGGGGGCCGCCTTCGCCACCGGTATTCCTCCA-GATCTCTACGCATTTCACCGCTAC ACCTGGAATTC-TACCCCCCTCTACGAGACTCTAGCTTGCCA-GTTTCAAATGCAG TTCCCAGGTTGAGCCCGGGGATTTCACATCTGACT-TAACAAACCGCCTGCGTGCGCTT TACGCCCAG-TAATTCCGATTAACGCTTGCACCCTCCGTATTAC-CGCGGCTGCTGGCAC GGAGTTAGCCGGTGCTTCTTCTGCGAGTAACGT-CAATTGATGAGCGTATTAAGCTCA CCACCTTCCTC-CTCGCTGAAAGTGCTTTACAACCCGAAGGCCTTCT-TCACACACGCGG CATGGCTGCATCAGGCTTGCGCCCATTGTGCAATAT-TCCCCACTGCTGCCTCCCGTAG GAGTCTGGACCGT-GTCTCAGTTCCAGTGTGGCTGGTCATCCTCTCA-GACCAGCTAGG GATCGTCGCCTAGGTGAGCCATTACCCCAC-CTACTAGCTAATCCCATCTGGGCACATC TGATG-GCAAGAGGCCCGAAGG (SEQ ID NO: 1).

The fatty acids analysis compared the differences between the composition of the cell walls in different bacteria, and this test showed that no conclusion could be reached as to the identification of the bacteria (Table 2):

ECL Deviation: 0.003
Total Response: 221425 Reference ECL Shift: 0.005
Percent Named: 96.57% Total Named: 213831

| Matches: | Total Amount: 200727 | Number Reference Peaks: 7 |
|---|---|---|
| Library | Sim Index | Entry Name |
| RTSBA6 6.10 | 0.687 | *Cedecea davisae* |
|  | 0.570 | *Cedecea neteri* |
|  | 0.547 | *Cedecea lapagei* |

-continued

| | | |
|---|---|---|
| ECL Deviation: 0.003 | | |
| Total Response: 221425 Reference ECL Shift: 0.005 | | |
| Percent Named: 96.57% Total Named: 213831 | | |
| Matches: | Total Amount: 200727 | Number Reference Peaks: 7 |
| Library | Sim Index | Entry Name |
| | 0.544 | *Escherichia coli* GC subgroup D (DNA homology with *Shigella*) |
| | 0.535 | *Salmonella bongori/enterica* |
| | 0.496 | *Salmonella enterica-enterica* E |
| | 0.470 | *Klebsiella pneumoniae-pneumoniae*-GC subgroup A |
| | 0.467 | *Enterobacter aerogenes* GC subgroup B |
| | 0.466 | *Serratia rubidaea* |
| | 0.447 | *Escherichia coli* GC subgroup G (DNA homology with *Shigella*) |

NRRL B-50575 differs from the type strain of *S. marcescens* in the composition of fatty acids and their abundance, with major differences being that *S. marcescens* type strain has 15:0 and 18:0 fatty acids but NRRL B-50575 does not. NRRL B-50575 has about 4 times as much 14:0 fatty acid in its cell wall compared to *S. marcescens* ATCC13880 and about 3 times as much 16:1 fatty acid, as well as about $2/10^{th}$ as much 17:1, about $1/3^{rd}$ as much cylo 17:0, and about ½ as much cyclo 19:0 (Table 3).

Isolation of TPSB-07-1 and TPSB-07-2: Bacteria were recovered in pure culture from 2 different insects that had died when fed NRRL B-50575 on freeze dried pellets. These bacteria were then compared to NRRL B-50575. Phenotypic tests showed that these recovered bacteria were nearly identical to NRRL B-50575, thus showing that the NRRL B-50575 had killed these insects (Tables 4, 6, 7 and 8).

Because of the results from the rRNA gene test, several of the tests done on NRRL B-50575 were also done on BF1 (a laboratory strain of *S. marcescens*) initially and later on ATCC-13880 (the type strain for *S. marcescens*) so that the results could be compared. Several biochemical profiles produced interesting results, and, with regard to the 96 different substrates in the Biolog system GP system (the pluses are oxidation based on oxidation of tetrazolium purple), there were 20 differences between NRRL B-50575 and BF1 as shown in Table 4 (bolded differences (L-aspartic acid through uridine) are differences between the original strain and those recovered from stink bugs treated with NRRL B-50575; strains NRRL B-50575, TPSB-08 and TPSB-09 were originally isolated from dead stink bugs; TPSB-07-1 and TPSB-07-2 were isolated from separate stink bugs that had died after feeding on TPSB-07. For each difference, NRRL B-50575 did not oxidize a substrate whereas BF1 did. NRRL B-50575 also produced lipase on egg yolk agar, while BF1 and ATCC 13880 did not. ATCC 13880 also did not produce a urease.

Antibiotic susceptibility tests were done to both NRRL B-50575 and BF1, and as with the biochemical profiles, the results were compared. Undergoing the same tests as NRRL B-50575, TPSB-08, TPSB-09 and BF1, both TPSB-07-1 and TPSB-07-2 produced the same results as NRRL B-50575, with the exception of 7 (out of 96) differences in the Biolog test using GP plates. In each of these differences, NRRL B-50575, TPSB-08, TPSB-09 each tested negative; while TPSB-07-1, 2 tested positive (for oxidizing succinic acid, D-fructose, D-trehalose, mono-methyl succinate, β-hydroxylbutyric acid, and uridine). For the fermentation tests/sugar inoculation, NRRL B-50575, TPSB-08, TPSB-09 made acid from arabinose, glucose, mannitol, xylose, sucrose, salicin, mannose, melibiose, trehalose, fructose, galactose, and maltose. The bacteria hydrolyzed esculin and did not make an acid from lactose or cellobiose. While the bacteria did make urease (which BF1 and ATCC-13880 did not) and protease (which ATCC-13880 did not), NRRL B-50575 did not make phospholipase, amylase, or hemolysin, neither did BF1 and ATCC-13880; the phospholipase, amylase, hemolysin, and protease tests were done at 25° C. The GEN III Biolog plates show three major differences between the strains. NRRL B-50575 grew on D-galactose and D-serine as sole carbon sources while ATCC 13880 did not. TPSB also was resistant to D-serine addition to a rich media, and BF1 and ATCC 13880 did not grow in the presence of D-serine. There were also 24 minor differences in degrees of growth between NRRL B-50575 and ATCC 13880. 63 tests were the same for all strains.

Figure 4:
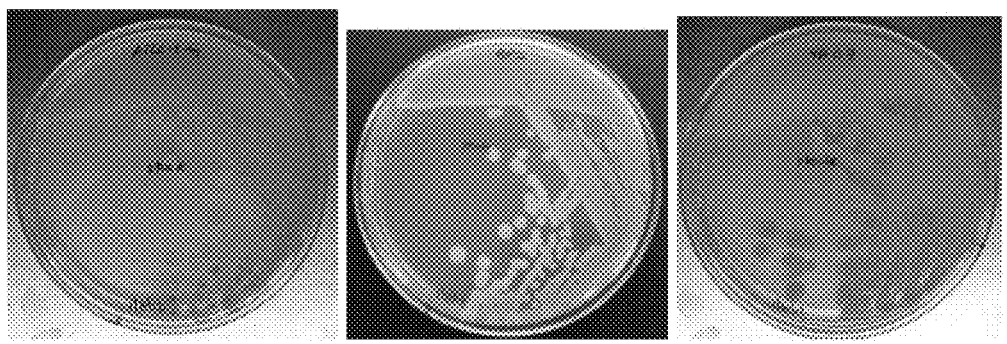
FIG. 4 shows pigment production by NRRL B-50575 (right), *Serratia marscesens* ATCC 13880 (left) and *Serratia marcescens* strain BF1 (center) as described below.

The diffusible pink pigment (FIG. 4) produced by NRRL B-50575 (TP 07) was different from the red pigment of BF1 and ATCC 13880 (ATCC-SM), and the pigment was made at temperatures below 25° C. Antibiotic susceptibility was determined using the disk method per manufacturer's instructions on L-agar, incubated at 25° C. (Table 6). All of the pink bacterial strains had the similar antibiotic resistance. They differed in sensitivity to tetracycline, kanamycin, and chloramphenicol. They also differed from BF1 and ATCC 13880 in sensitivity to erythromycin.

Figure 5:
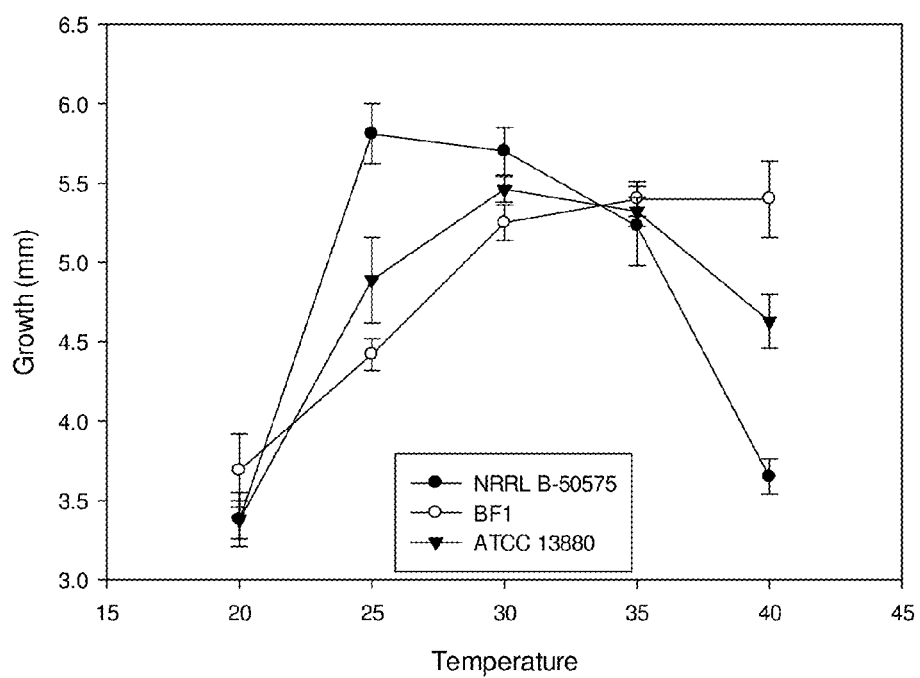
FIG. 5 shows bacterial temperature optima as described below.

FIG. 5 (n=18) shows the difference in optimal temperature growth of NRRL B-50575 and BF1 and ATCC 13880. The optimal temperature for growth for NRRL B-50575 is 25° C., while for BF1 it is 35° C. and ATTC13880 it is 30° C. NRRL B-50575 grows at pH 4 while BF1 and ATCC 13880 do not.

Figure 6:
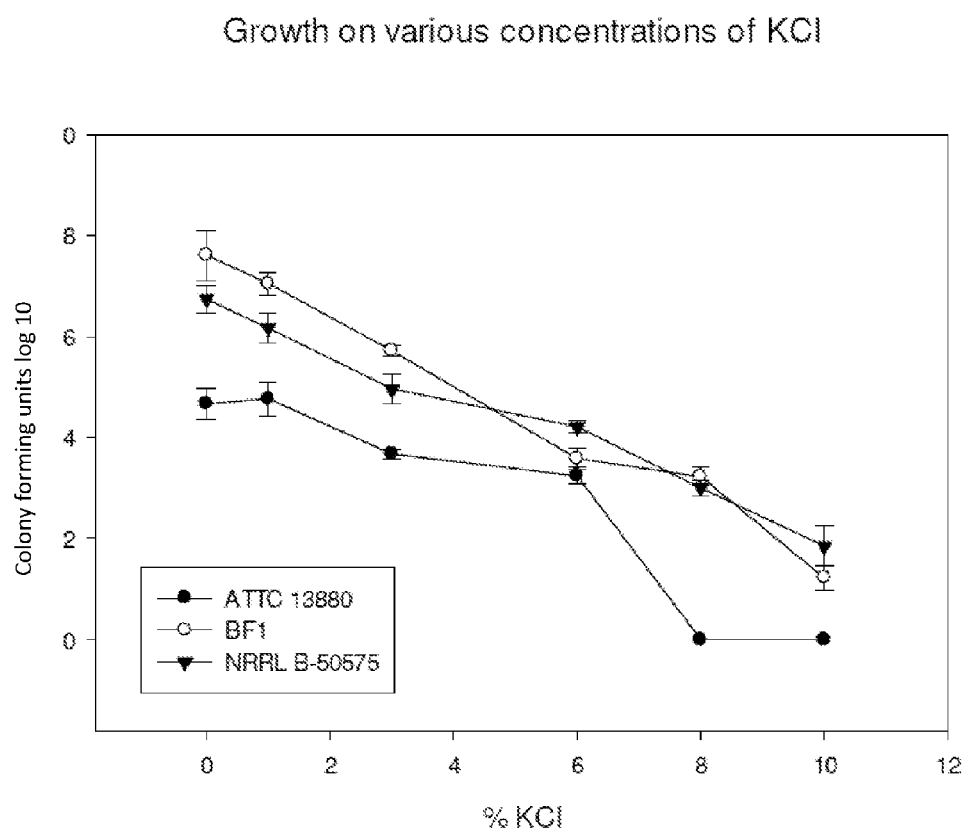
FIG. 6 shows bacterial growth on KCl as described below.

While the growth of all three strains was different at all concentrations of KCl, at 48 h the ATCC type strain did not grow on 8% KCl while the bacterial strains isolated from insects grew at this concentration, n=9 (FIG. 6).

Table 7 shows differences in pigment formation among the strains. Most notable was the difference in pigment formation due to aeration. The type strain ATCC-13880 only made pigment in still culture while BF1 made pigment in shaken culture, but NRRL B-50575 only made pigment under high aeration conditions (with increased shaking form 125 rpm to 250 rpm). The spectral properties of the pigments also differed with NRRL B-50575 having peaks at 605, 510, and 410 nm; BF1 had peaks at 605, 510, 405 and 365 nm, while the type strain had peaks at 385 and 365 nm.

NRRL B-50575 made a urease. The ATTC strain did not make a urease under any conditions tested. BF1 only turned the weakly buffered urease medium pink indicating a change in pH (Table 8).

In late July and August, other stink bugs brought into the lab died quickly and bacteria were isolated from 20 insects. Three insects yielded no culturable bacteria while other insects yielded most mixed cultures with 1×10³ to 6.8×10⁸ bacteria recovered per insect (Table 9). Only one of these bacteria (TPSB-160) appeared similar to NRRL B-50575 by colony morphology but on further testing differed from this strain (Tables 7 and 8). This indicated that NRRL B-50575 was not common.

Discussion: Because of the discovery of NRRL B-50575, we are provided with a naturally occurring pathogen for BMSB. The discovery of NRRL B-50575 seems to have been by complete serendipity. When *C. subtsugae* was the initial pathogen to be used, stink bugs to test the pathogen on were first needed. There were no stink bugs available from the colony being raised in the lab, so the only other option was the use of field collected stink bugs. 30 or so stink bugs were collected each night in a single, communal container. After about 12 hours, the majority of the stink bugs would be dead, and many of these dead insects had crimson abdomens. During the previous 12 hours, all of the captured insects seemed alive and well, so these deaths were unexpected. Because the natural color of the BMSB's abdomen is a tan hue, the crimson abdomens also stood out; what stood out even more was the fact that almost every single one of the insects with a crimson abdomen was male. Prior to this phenomenon, bacteria from 2 live stink bugs had been isolated and in the case of both insects 3 separate types of bacteria were recovered (confirmed by 16S rRNA sequencing and biochemical profiles). In order to determine whether or not the insect deaths and the crimson abdomens were related to a pathogen, the same procedure then used to isolate bacteria from the gut of the BMSB was done on 3 dead insects that were collected the night before. The results of this isolation procedure yielded pure cultures of a pink bacterium. The recovery of the bacteria in pure culture was an indication that this particular bacterium was pathogenic, and Koch's postulates were used to confirm this. The bacteria isolated from the dead stink bugs (NRRL B-50575) surprisingly did kill other stink bugs and it was almost identical to TPSB-07-1 and TPSB-07-2 (Table 1).

The fact that the BMSB feeds on an artificial diet intended for the southern corn rootworm was unexpected and allowed for a controlled delivery of the bacteria to BMSB. Additional testing of survival of nymphs suggested that other insect diets including diamondback moth diet could be used for delivery of NRRL B-50575. Further experimentation showed that non-feeding BMSB could survive for at least 2 months on dental wicks which had been rehydrated with sterile water. Either way is a method to test bacterial, viral, or chemical suspensions/solutions to the BMSB by feeding.

From a visual perspective, NRRL B-50575 resembled BF1 in the way it looked and grew, but to actually determine the identity of the pathogen, the bacterial identification procedures were done. While the 16S rRNA sequencing results identified NRRL B-50575 as *S. marcescens*, a variety of differences have been noted between the two. The pigment produced by NRRL B-50575 (FIG. 8) seems to be Ferrorosamine, which diffused into the growth medium (Feister, G. H, et al., Ferrorosamine A from *Erwinia rhapontici*, Curr. Microbiol., 8: 239-243 (1983)), and was produced at temperatures under 25° C., while BF1 produced red prodigiosin which was retained within the bacterial cell. Ferrorosamine sequesters iron, and it may be involved with the mortality of the insects. When grown at a higher temperature, NRRL B-50575 does not produce the pigment and does not kill. In addition to this, plant ureases, have been known to show insecticidal properties (Carlini, C. R., and J. C. Polacco. Crop Protect., 48: 1665-1672 (2008)).

26 differences between NRRL B-50575 and BF1 were recorded in the Biolog system, it can be concluded that NRRL B-50575 is not a typical *Serratia marcescens* or is a new species.

All of the references cited herein, including U.S. Patents, are incorporated by reference in their entirety. Also incorporated by reference in their entirety are the following references: Bucher, G. G., Identification of bacteria found in insects, In: Microbial control of pests and plant diseases 1970-1980, H. D. Burges (ed.), Academic Press. New York, 1981); Endo, N., et al., J. Chem. Ecol., 32: 1605-1612 (2006); Grimont, P. A. D., et al., Intern. J. System. Bacteriol., 38:1-6 (1988); Hall, A, 1999, Costly Interlopers. http://www.scientificamerican.com/article.cfm?id=costly-interlopers accessed 9/29/11; Samrot, A. V., et al., Intern. Res. J. Biotechnol., 2:128-133 (2011); Tindall, B. J., et al., Intern. J. System. Evolut. Microbiol., 66: 249-266 (2010); Williams, R. P., Appl. Microbiol., 396-402 (1973); U.S. Pat. No. 7,244,607; EPA Home Page, 2011, http://www.epa.gov/pesticides/controlling/stinkbugs/accessed 9/28/11); Rice Mahr, S. E., et al., Biological control of insects and other pests of greenhouse crops, Cooperative Extension Publication NCR581, U. Wisconsin, Madison, Wis., 2001).

Thus, in view of the above, the present invention concerns (in part) the following:

An insect biocontrol agent comprising a biologically pure *Serratia* strain wherein said strain has the following characteristics: produces diffusible pigment, grows on D-serine and D-galactose as sole carbon source, makes acid from trehalose, pigment not produced by growth on sugars, produces urease and lipase, and pathogenic to *Halyomorpha halys*.

An insect biocontrol agent consisting essentially of a biologically pure *Serratia* strain having all of the identifying characteristics of *Serratia* strain NRRL B-50575.

An agricultural biocontrol composition consisting essentially of a biologically pure *Serratia* strain having all of the identifying characteristics of *Serratia* strain NRRL B-50575, and optionally an agriculturally acceptable carrier.

A method for killing insects, comprising treating or exposing an object or area with an insect killing effective amount of an agricultural biocontrol composition containing a biologically pure *Serratia* strain having all of the identifying characteristics of *Serratia* strain NRRL B-50575, and optionally a carrier or carrier material.

An isolated strain of *Serratia*, strain NRRL B-50575 or a variant thereof which is capable of killing *Halyomorpha halys*. A biologically pure culture of *Serratia* having all the identifying characteristics of strain NRRL B-50575, wherein said identifying characteristics include produces diffusible pigment, grows on D-serine and D-galactose as sole carbon source, makes acid from trehalose, pigment not produced by growth on sugars, produces urease and lipase, and pathogenic to *Halyomorpha halys*. An insect biocontrol agent comprising the biologically pure strain of *Serratia* described above wherein said strain produces diffusible pigment, grows on D-serine and D-galactose as sole carbon source, makes acid from trehalose, pigment not produced by growth on sugars, produces urease and lipase, and pathogenic to *Halyomorpha halys*.

A composition comprising an isolated *Serratia* (NRRL B-50575) or an isolated strain having all of the identifying characteristics of the *Serratia* (NRRL B-50575).

An isolated strain of *Serratia*, strain NRRL B-50575, which is capable of killing *Halyomorpha halys*.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Comparison of ingredients of freeze-dried diets

| Ingredient | Type of diet g/l | | |
|---|---|---|---|
| | Tobacco hornworm | Diamondback moth | Corn rootworm |
| Wheat germ | 40 | 83.5 | 27.5 |
| Casein | 35 | 31.5 | 32 |
| Sucrose | 35 | 31 | 32 |
| Brewer's yeast | 10 | | |
| Wesson salts | 10 | 9 | 9 |
| USDA Vitamin mix | 5 | | |
| Vanderant vitamin mix | | 9 | 15 |
| Ascorbic acid | 4 | | |
| Sorbic acid | 2 | 1 | .75 |
| Methyl-paraben | 1 | 1.4 | 1 |
| Cholesterol | | | .06 |
| Linseed oil | | | .25 |
| 10% KOH | | | 10 |
| Celarlin | | 17.5 | |
| Benlate | | 17.9 | |
| Alphacel | | | 14 |
| Agar | 15 | 17.5 | 14.5 |
| water | 850 ml | 750 | 800 |

TABLE 2

Fatty acid composition of NRRL B-50575

| RT | Response | Ar/Ht | RFact | ECL | Peak Name | Percent | Comment1 | Comment2 |
|---|---|---|---|---|---|---|---|---|
| 0.7330 | 115074 | 0.006 | — | 6.5631 | | — | <min rt | |
| 0.7453 | 1.033E+9 | 0.023 | — | 6.6470 | SOLVENT PEAK | — | <min rt | |
| 1.2349 | 548 | 0.012 | 1.191 | 10.001 | 10:0 | 0.33 | ECL deviates 0.001 | Reference 0.004 |
| 1.4119 | 916 | 0.010 | 1.128 | 10.951 | Sum In Feature 2 | 0.51 | ECL deviates −0.002 | unknown 10.9525 |
| 1.6063 | 3150 | 0.010 | — | 11.817 | unknown 11.825 | — | ECL deviates −0.008 | |
| 1.6476 | 5929 | 0.010 | 1.070 | 11.998 | 12:0 | 3.16 | ECL deviates −0.001 | Reference 0.005 |
| 1.9674 | 2632 | 0.009 | 1.017 | 13.204 | 12:0 2OH | 1.33 | ECL deviates 0.001 | |
| 2.1478 | 1810 | 0.009 | — | 13.832 | | — | | |
| 2.1830 | 1775 | 0.008 | — | 13.955 | unknown 13.951 | — | ECL deviates 0.004 | |
| 2.1955 | 9086 | 0.009 | 0.988 | 13.998 | 14:0 | 4.47 | ECL deviates −0.001 | Reference 0.006 |
| 2.3532 | 1905 | 0.010 | — | 14.518 | unknown 14.502 | — | ECL deviates 0.002 | |
| 2.4992 | 1122 | 0.009 | — | 14.999 | 15:0 | — | ECL deviates −0.001 | |
| 2.5535 | 1068 | 0.009 | — | 15.172 | | — | | |
| 2.5728 | 6878 | 0.009 | 0.953 | 15.234 | 14:0 2OH | 3.26 | ECL deviates 0.001 | |
| 2.6605 | 20418 | 0.009 | 0.946 | 15.515 | Sum In Feature 2 | 9.63 | ECL deviates 0.000 | 14:0 3OH/16:1 iso I |
| 2.7611 | 31237 | 0.009 | 0.939 | 15.836 | Sum In Feature 3 | 14.62 | ECL deviates −0.003 | 16:1 w7c/16:1 w6c |
| 2.8115 | 66532 | 0.009 | 0.936 | 15.998 | 16:0 | 31.03 | ECL deviates −0.002 | Reference 0.003 |
| 2.8416 | 1388 | 0.013 | — | 16.094 | | — | | |
| 3.0757 | 393 | 0.010 | 0.922 | 16.842 | 17:1 w7c | 0.18 | ECL deviates 0.007 | |
| 3.0989 | 26652 | 0.009 | 0.920 | 16.916 | 17:0 cyclo | 12.22 | ECL deviates 0.002 | |
| 3.1258 | 1083 | 0.009 | 0.919 | 17.002 | 17:0 | 0.50 | ECL deviates 0.003 | Reference 0.005 |
| 3.2963 | 665 | 0.009 | 0.912 | 17.551 | 16:0 3OH | 0.30 | ECL deviates 0.004 | |
| 3.3595 | 1188 | 0.010 | 0.909 | 17.755 | Sum In Feature 5 | 0.54 | ECL deviates −0.001 | 18:2 w6,9018:0 ante |
| 3.3881 | 32410 | 0.009 | 0.908 | 17.847 | Sum In Feature 8 | 14.67 | ECL deviates 0.000 | 18:1 w7c |
| 3.4370 | 889 | 0.010 | 0.907 | 18.004 | 18:0 | 0.40 | ECL deviates 0.005 | Reference 0.004 |
| 3.5798 | 1912 | 0.011 | — | 18.475 | | — | | |
| 3.6482 | 872 | 0.011 | — | 18.700 | | — | | |
| 3.7203 | 5659 | 0.009 | 0.899 | 18.938 | 19:0 cyclo w8c | 2.53 | ECL deviates 0.006 | |
| 3.7377 | 717 | 0.010 | 0.898 | 18.995 | 19:0 | 0.32 | ECL deviates −0.004 | Reference −0.009 |
| 3.7880 | 544 | 0.013 | — | 19.164 | | — | | |
| — | 21334 | — | — | — | Summed Feature 2 | 10.14 | 12:0 aldehyde ? 16:1 iso I/14:0 3OH | unknown 10.9525 14:0 3OH/16:1 iso I |
| — | 31237 | — | — | — | Summed Feature 3 | 14.62 | 16:1 w7c/16:1 w6c | 16:1 w6c/16:1 w7c |
| — | 1188 | — | — | — | Summed Feature 5 | 0.54 | 18:0 ante/18:2 w6,9c | 18:2 w6,9c/18:0 ante |
| — | 32410 | — | — | — | Summed Feature 8 | 14.67 | 18:1 w7c | 18:1 w6c |

TABLE 3

Comparison of fatty acid composition of NRRL B-50575 and ATCC 13880

| | Strain (%) | |
|---|---|---|
| Fatty acid | NRRL B-50575 | ATCC13880 |
| 14:0 | 4.47 | 1.2 |
| 15:0 | 0 | trace |
| 16:0 | 31.03 | 43.2 |
| 16:1 | 14.62 | 5.2 |
| 17:1 | 0.18 | 1.0 |
| Cyclo 17:0 | 12.2 | 31.4 |
| 18:0 | 0 | 1.2 |
| 18:1 | 14.67 | 11.0 |
| Cyclo 19:0 | 2.53 | 5.4 |

TABLE 4

Differences between pink bacteria and *S. marcescens* BF1

| | Strains | | | | | |
|---|---|---|---|---|---|---|
| Chemical | NRRL B-50575* | TPSB-08* | TPSB-09* | TPSB-07-1* | TPSB-07-2* | BF1* |
| α-cyclodextrin | − | − | − | − | − | + |
| D-arabitol | − | − | − | − | − | + |
| i-erythritol | − | − | − | − | − | ++ |
| α-lactose | − | − | − | − | − | + |
| α-D-lactose lactulose | − | − | − | − | − | + |
| L-rhamnose | − | − | − | − | − | + |
| turanose | − | − | − | − | − | + |

TABLE 4-continued

Differences between pink bacteria and *S. marcescens* BF1

| Chemical | NRRL B-50575* | TPSB-08* | TPSB-09* | TPSB-07-1* | TPSB-07-2* | BF1* |
|---|---|---|---|---|---|---|
| D-galactonic acid lactone | − | − | − | − | − | + |
| D-glucosaminic acid | − | − | − | − | − | + |
| α-hydroxy butyric acid | − | − | − | − | − | + |
| α-keto butyric acid | − | − | − | − | − | + |
| α-keto glutaric acid | − | − | − | − | − | + |
| propionic acid | − | − | − | − | − | + |
| alaninamide | − | − | − | − | − | ++ |
| glycyl-L-aspartic acid | − | − | − | − | − | ++ |
| glycyl-L-glutamic acid | − | − | − | − | − | ++ |
| L-ornithine | − | − | − | − | − | ++ |
| L-phenyl alanine | − | − | − | − | − | ++ |
| L-threonine | − | − | − | − | − | + |
| phenyl ethylamine | − | − | − | − | − | + |
| L-aspartic acid | − | − | − | + | + | ++ |
| succinic acid | − | − | − | + | − | + |
| D-trehalose | − | − | − | + | + | ++ |
| mono-methyl succinate | − | − | − | + | + | + |
| β-hydroxy butyric acid | − | − | − | + | + | ++ |
| uridine | − | − | − | + | + | ++ |

TABLE 5

Comparison of NRRL B-50575, BF1 and ATCC 13880 using GEN III MicroPlate ™
(major differences are in bold italics)

| | NRRL B-50575 | BF1 | ATCC 13880 |
|---|---|---|---|
| A1 Negative Control | − | − | − |
| A2 Dextrin | +/− | +/− | − |
| A3 D-Maltose | + | +/− | +/− |
| A4 D-Trehalose | +/− | +/− | +/− |
| A5 D-Cellobiose | − | − | − |
| A6 Gentiobiose | − | − | − |
| A7 Sucrose | +/− | + | +/− |
| A8 D-Turanose | − | − | − |
| A9 Stachyose | − | − | − |
| A10 Positive Control | + | + | + |
| A11 pH 6 | + | + | + |
| A12 pH 5 | + | + | + |
| B1 D-Raffinose | − | − | − |
| B2 α-D-Lactose | − | − | − |
| B3 D-Melibiose | +/− | − | − |
| B4 β-Methyl-DGlucoside | +/− | +/− | +/− |
| B5 D-Salicin | +/− | + | +/− |
| B6 N-Acetyl-DGlucosamine | + | + | + |
| B7 N-Acetyl-β-DMannosamine | +/− | + | +/− |
| B8 N-Acetyl-DGalactosamine | + | +/− | + |
| B9 N-Acetyl Neuraminic Acid | − | − | − |
| B10 1% NaCl | + | + | + |
| B11 4% NaCl | +/− | +/− | +/− |
| B12 8% NaCl | − | − | − |
| C1 α-D-Glucose | +/− | +/− | +/− |
| C2 D-Mannose | +/− | +/− | +/− |
| C3 D-Fructose | + | +/− | +/− |
| C4 D-Galactose | + | + | − |
| C5 3-Methyl Glucose | +/− | +/− | +/− |
| C6 D-Fucose | + | +/− | +/− |
| C7 L-Fucose | + | + | + |
| C8 L-Rhamnose | − | − | − |
| C9 Inosine | +/− | +/− | +/− |
| C10 1% Sodium Lactate | + | + | + |
| C11 Fusidic Acid | +/− | − | − |
| C12 D-Serine | + | + | − |
| D1 D-Sorbitol | +/− | +/− | +/− |
| D2 D-Mannitol | +/− | +/− | +/− |
| D3 D-Arabitol | +/− | − | − |
| D4 myo-Inositol | + | + | + |
| D5 Glycerol | + | + | +/− |
| D6 D-Glucose-6-PO$_4$ | + | + | + |
| D7 D-Fructose-6-PO$_4$ | + | + | + |
| D8 D-Aspartic Acid | − | − | − |
| D9 D-Serine | + | + | − |
| D10 Troleandomycin | + | + | + |
| D11 Rifamycin SV | + | + | + |
| D12 Minocycline | − | − | − |
| E1 Gelatin | + | + | +/− |
| E2 Glycyl-L-Proline | + | + | + |
| E3 L-Alanine | + | + | + |
| E4 L-Arginine | +/− | +/− | +/− |
| E5 L-Aspartic Acid | + | + | + |
| E6 L-Glutamic Acid | + | + | + |
| E7 L-Histidine | + | + | + |
| E8 L-Pyroglutamic Acid | − | − | − |
| E9 L-Serine | + | + | + |
| E10 Lincomycin | + | + | + |
| E11 Guanidine HCl | +/− | +/− | +/− |
| E12 Niaproof 4 | + | + | + |
| F1 Pectin | +/− | +/− | +/− |
| F2 D-Galacturonic Acid | + | + | + |
| F3 L-Galactonic Acid Lactone | − | − | − |
| F4 D-Gluconic Acid | + | +/− | + |
| F5 D-Glucuronic Acid | + | + | + |
| F6 Glucuronamide | + | + | +/− |
| F7 Mucic Acid | − | − | − |
| F8 Quinic Acid | − | − | − |
| F9 D-Saccharic Acid | − | − | − |
| F10 Vancomycin | + | + | + |
| F11 Tetrazolium Violet | + | + | + |
| F12 Tetrazolium Blue | + | + | + |
| G1 p-Hydroxy-Phenylacetic Acid | +/− | +/− | +/− |
| G2 Methyl Pyruvate | +/− | +/− | +/− |
| G3 D-Lactic Acid Methyl Ester | − | − | − |
| G4 L-Lactic Acid | + | + | + |
| G5 Citric Acid | + | + | + |
| G6 α-Keto-Glutaric Acid | + | +/− | +/− |
| G7 D-Malic Acid | +/− | +/− | + |
| G8 L-Malic Acid | + | + | + |
| G9 Bromo-Succinic Acid | +/− | +/− | +/− |
| G10 Nalidixic Acid | − | − | − |
| G11 Lithium Chloride | +/− | +/− | +/− |
| G12 Potassium Tellurite | − | − | − |
| H1 Tween 40 | +/− | +/− | +/− |
| H2 γ-Amino-Butryric Acid | +/− | +/− | + |
| H3 α-Hydroxy-Butyric Acid | − | − | +/− |
| H4 β-Hydroxy-D,L-Butyric Acid | +/− | +/− | + |
| H5 α-Keto-Butyric Acid | +/− | +/− | − |
| H6 Acetoacetic Acid | + | + | +/− |
| H7 Propionic Acid | +/− | − | − |
| H8 Acetic Acid | +/− | +/− | + |
| H9 Formic Acid | +/− | +/− | − |
| H10 Aztreonam | +/− | +/− | +/− |
| H11 Sodium Butyrate | +/− | +/− | +/− |
| H12 Sodium Bromate | − | − | − |

TABLE 6

Antibiotic resistance of NRRL B-50575, TPSB-08, TPSB-09 compared to *Serratia marcesans* BF1 and ATCC 13880

| Antibiotic | NRRL B-50575 | TBSB-08 | TBSB-09 | BF1 | ATCC 13880 |
|---|---|---|---|---|---|
| Ampicillin | R | R | R | R | R |
| Vancomycin | R | R | R | R | R |
| Erythromycin | R | R | R | I | I |
| Triple sulfa | R | R | R | R | R |
| Tetracycline | I | I | R | R | R |
| Kanamycin | S | I | S | S | S |
| Neomycin | S | S | S | S | S |
| Chloramphenicol | I | I | S | S | I |

R—Resistant
I—Intermediate
S—Susceptible

TABLE 7

Pigment production in various strains

| Medium | Temp | NRRL B-50575 | TPSB 08 | TPSB 09 | TPSB 7-1 | TPSB 7-2 | TPSB 160 | BF1 | ATCC-13880 |
|---|---|---|---|---|---|---|---|---|---|
| L agar 0.5% NaCl | 4 | − | − | − | − | − | − | − | − |
| L agar 0.5% NaCl | 20 | +* | − | +* | +* | +* | − | | |
| L agar 0.5% NaCl | 25 | +* | +* | +* | +* | +* | − | + | + |
| L agar 0.5% NaCl | >30 | − | − | − | −* | − | − | +/− | + pink |
| L agar 0% KCl, 0% NaCl | 25 | +* | +* | +* | +* | +* | | + | + |
| | 30 | +* | +* | +* | +* | +* | − | +/− | + |
| L agar 1% KCl | 25 | +* | +* | +* | +* | +* | − | + | + |
| L agar >3% KCl | 25 | − | − | − | − | − | − | + | + |
| L broth pH 7.915 | 25 | − | | | | | | + faint | |
| L broth 0 rpm | 25 | | | | | | | − | + |
| pH 7   125 rpm | | | | | | | | + | − |
|       250 rpm | 25 | + | | | | | | − | + pink |
| L broth pH <5.0 | 25 | − | | | | | | − | − |
| Minimal glucose agar | 25 | − | − | − | − | − | − | + | + (weak) |
| Sugar agar: Me, La, Ga, Ar, Sa, Es, Ma | 25 | − | − | − | − | − | − | − | − |
| Sugar agar: Tr, Fr, Su | 25 | − | − | − | − | − | − | + | + |

*pigment is diffusible into the medium.
Sugar abbreviations: Me — melibose, La — lactose, Ga — galactose, Ar — arabinose, Sa — Salicin, Es — esculin Ma — mannose, Tr — rehalose, Fr — fructose, Su — sucrose.

TABLE 8

Urease Broth Results

| | Urea-Peptone 0.015M phosphate | Urea-Yeast Extract 0.12M phosphate | Urea-Yeast Extract 0.015M phosphate | Urea-Peptone 0.12M phosphate |
|---|---|---|---|---|
| NRRL B-50575 | pink + | pink | pink − | faint orange/pink + |
| TPSB 7-2 | pink + | pink | pink − | faint orange/pink + |
| TPSB09 | pink + | pink | faint pink − | faint orange/pink + |
| TPSB-08 | pink + | orange/pink | light orange − | light orange + |
| TPSB 7-1 | pink + | light orange | light orange − | light orange + |
| BF1 | pink + | light orange | light orange − | light orange + |
| TP 160 | light orange + | light orange | light orange − | light orange + |
| ATCC-13880 | light orange + | light orange | light orange − | light orange + |
| Control | light orange − | light orange − | light orange − | light orange − |

+ turbidity

TABLE 9

Isolation of bacteria from dead stink bugs

| Stink bug number | Titer | Gram strain |
|---|---|---|
| 13 | $1 \times 10^3$ | Nd |
| 19 | $2.4 \times 10^7$ | − |
| 24 | $1.16 \times 10^6$ | Multiple types |
| 57 | $3 \times 10^5$ | + |
| 65 | $2.5 \times 10^3$ | + |
| 90 | $6.8 \times 10^8$ | + |
| 97 | $7.5 \times 10^8$ | Mixed |
| 106 | $2.35 \times 10^7$ | 3 types |
| 107 | $1.96 \times 10^6$ | 3 types |
| 114 | $9.8 \times 10^5$ | + |
| 115 | $2.65 \times 10^6$ | + |
| 116 | $2 \times 10^7$ | |
| 128 | $7.48 \times 10^6$ | + |
| 130 | $3 \times 10^8$ | Mix |
| 136 | $4 \times 10^7$ | + |
| 137 | $2.3 \times 10^5$ | + |
| 146 | $5.1 \times 10^6$ | + |

We claim:

1. A method for killing insects, comprising treating an object or area with an insect killing effective amount of a composition comprising a biologically pure culture of *Serratia* strain NRRL B-50575, and optionally a carrier or carrier material; wherein the identifying characteristics of *Serratia* strain NRRL B-50575 include produces diffusible pigment, grows on D-serine and D-galactose as sole carbon source, makes acid from trehalose, pigment not produced by growth on sugars, produces urease and lipase, and pathogenic to *Halyomorpha halys*; wherein said insects are *Halyomorpha halys*.

2. The method according to claim 1, wherein said identifying characteristics of *Serratia* strain NRRL B-50575 include no oxidation of α-cyclodextrin, D-arabitol, i-erythritol, α-lactose, α-D-lactose lactulose, L-rhamnose, turanose, D-galactonic acid lactone, D-glucosaminic acid, α-hydroxy butyric acid, α-keto butyric acid, α-keto glutaric acid, propionic acid, alaninamide, glycyl-L-aspartic acid, glycyl-L-glutamic acid, L-ornithine, L-phenyl alanine, L-threonine, phenyl ethylamine, L-aspartic acid, succinic acid, D-trehalose, mono-methyl succinate, α-hydroxy butyric acid, and uridine.

3. The method according to claim 1, wherein the spectral properties of said diffusible pigment are peaks at 605, 510, and 410 nm.

* * * * *